US012797421B2

(12) United States Patent
Rosenberg et al.

(10) Patent No.: US 12,797,421 B2
(45) Date of Patent: Nov. 17, 2026

(54) BACTERIA FOR THE PREVENTION AND TREATMENT OF SMOKE-INDUCED LUNG DAMAGE

(71) Applicant: Biomuse Ltd., Givat Shmuel (IL)

(72) Inventors: Eugene Rosenberg, Givat Shmuel (IL); Ilana Zilber-Rosenberg, Givat Shmuel (IL); Ophir Levy, Givat Shmuel (IL)

(73) Assignee: Biomuse Ltd., Givat Shmuel (IL)

( * ) Notice: Subject to any disclaimer, the term of this patent is extended or adjusted under 35 U.S.C. 154(b) by 775 days.

(21) Appl. No.: 17/914,783

(22) PCT Filed: Mar. 31, 2021

(86) PCT No.: PCT/IL2021/050366

§ 371 (c)(1),
(2) Date: Sep. 27, 2022

(87) PCT Pub. No.: WO2021/199047

PCT Pub. Date: Oct. 17, 2021

(65) Prior Publication Data

US 2024/0000857 A1 Jan. 4, 2024

Related U.S. Application Data

(60) Provisional application No. 63/002,611, filed on Mar. 31, 2020.

(51) Int. Cl.

| | |
|---|---|
| ***A61K 35/74*** | (2015.01) |
| ***A61P 11/00*** | (2006.01) |
| ***C12N 1/20*** | (2006.01) |
| *A61K 35/00* | (2006.01) |

(52) U.S. Cl.

CPC .............. *A61K 35/74* (2013.01); *A61P 11/00* (2018.01); *C12N 1/20* (2013.01); *A61K 2035/11* (2013.01)

(58) Field of Classification Search

None

See application file for complete search history.

(56) References Cited

U.S. PATENT DOCUMENTS

| | | | |
|---|---|---|---|
| 2021/0069269 A1 | 3/2021 | Feuz et al. | |
| 2021/0074378 A1 | 3/2021 | Zhou et al. | |

FOREIGN PATENT DOCUMENTS

| | | | |
|---|---|---|---|
| CN | 101016529 | 8/2007 | |
| CN | 101428075 | 5/2009 | |
| CN | 101522193 | 9/2009 | |
| CN | 102433276 | 5/2012 | |
| CN | 104918624 | 9/2015 | |
| WO | WO 2014/078911 | 5/2014 | |
| WO | WO-2014096437 A1 * | 6/2014 | ................ A61P 9/10 |
| WO | WO 2019/018511 | 1/2019 | |
| WO | WO 2019/202033 | 10/2019 | |
| WO | WO 2021/199047 | 10/2021 | |

OTHER PUBLICATIONS

Seo, Jong-Su, Young-Soo Keum, and Qing X. Li. "Bacterial degradation of aromatic compounds." International journal of environmental research and public health 6.1 (2009): 278-309. (Year: 2009).*

CDC, retreived from https://www.cdc.gov/tobacco/about/index.html on Sep. 12, 2025 (Year: 2025).*

Thisted, Thomas, et al. "Optimization of a nicotine degrading enzyme for potential use in treatment of nicotine addiction." BMC biotechnology 19.1 (2019): 56. (Year: 2019).*

Atherton (Engineering the Human Lung Microbiome to Degrade Inhaled Carcinogens). (Year: 2018).*

Mouth microbes, retrieved from https://newsinhealth.nih.gov/2019/05/mouth-microbes on Sep. 18, 2025. (Year: 2019).*

Bamigbade, Gafar Babatunde, et al. "An updated review on prebiotics: insights on potentials of food seeds waste as source of potential prebiotics." Molecules 27.18 (2022): 5947. (Year: 2022).*

Antibiotics, retrieved from https://www.nhs.uk/medicines/antibiotics/#:~:text=There%20are%20hundreds%20of%20different,be%20classified%20into%206%20groups.&text=Other%20antibiotics%20include%20chloramphenicol%20(used,used%20for%20urinary%20tract%20infections). on Sep. 18, 2025 (Year: 2025).*

Machine Translation into English from Dec. 16, 2023 of Notification of Office Action and Search Report Dated Dec. 8, 2023 From the National Intellectual Property Administration of the People's Republic of China Re. Application No. 202180032355.7. (15 Pages).

Notification of Office Action and Search Report Dated Dec. 8, 2023 From the National Intellectual Property Administration of the People's Republic of China Re. Application No. 202180032355.7. (13 Pages).

Notification of Office Action and Search Report Dated May 16, 2024 From the State Intellectual Property Office of the People's Republic of China Re. Application No. 202180032355.7 and Its Machine Translation Into English. (23 Pages).

Summary Dated May 28, 2024 of Notification of Office Action and Search Report Dated May 16, 2024 From the State Intellectual Property Office of the People's Republic of China Re. Application No. 202180032355.7. (10 Pages).

International Search Report and the Written Opinion Dated Jun. 23, 2021 From the International Searching Authority Re. Application No. PCT/IL2021/050366. (18 Pages).

Abena et al. "Crude Oil Biodegradation by Newly Isolated Bacterial Strains and Their Consortium Under Soil Microcosm Experiment", Applied Biochemistry and Biotechnology, 189:1223-1244, Jun. 24, 2019.

Atherton et al. "Engineering the Human Lung Microbiome to Degrade Inhaled Carcinogens", PLOS Synthetic Biology, p. 1-16, Feb. 23, 2018.

(Continued)

*Primary Examiner* — Robert J Yamasaki
*Assistant Examiner* — Trevor Kane

(57) ABSTRACT

A method of treating or preventing a disease associated with smoke residue in a subject is disclosed. The method comprises administering to the subject a therapeutically effective amount of at least one agent which increases the amount of a bacterium which is capable of breaking down the smoke residue in the subject. Methods of alleviating the symptoms caused by withdrawal from the use of nicotine are also disclosed.

7 Claims, 9 Drawing Sheets

Specification includes a Sequence Listing.

(56) References Cited

OTHER PUBLICATIONS

Evsyutina et al. "Lung Microbiome in Healthy and Diseased Individuals", World Journal of Respirology, 7(2): 39-47, Jul. 28, 2017.
Feuz et al.
Geiss et al. "Tobacco, Cigarettes and Cigarette Smoke. An Overview", European Commission, Directorate-General, Joint Research Centre, Institute for Health and Consumer Protection, EUR 22783 EN, p. 1-74, 2007.
Le Noci et al. "Modulation of Pulmonary Microbiota by Antibiotic or Probiotic Aerosol Therapy: A Strategy to Promote Immunosurveillance Against Lung Metastases", Cell Reports, 24(13): 3528-3538, Sep. 25, 2018.
Ruan et al. "Studies on Microbiological Degradation of Tobacco Tar", Journal of Environmental Science and Health, Part A: Toxic/Hazardous Substances & Environmental Engineering, 40(11): 2073-2083, Nov. 2005.
Salgado-Brito et al. "Oxidation of Solid Paraffin (C11-40) By Pseudomonas Aeruginosa MGP-1", Annals of Microbiology, 57(3):321-328, Sep. 2007.
Sowada et al. "Degradation of Benzo[A]Pyrene by Bacterial Isolates From Human Skin", FEMS Microbiology Ecology, 88(1): 129-139, Published Online Jan. 21, 2014.
Tao et al. "Looking for Polycyclic Aromatic Hydrocarbon Metabolizing Microorganisms in the Oral Cavity of Smokers", Reprint From Research Square, p. 1-23, Oct. 1, 2021.
Van de Wiele et al. "Human Colon Microbiota Transform Polycyclic Aromatic Hydrocarbons to Estrogenic Metabolites", Environmental Health Perspectives, 113(1): 6-10, Published Online Sep. 22, 2004.
Zheng et al. "Characterization of Bacterial Composition and Diversity in a Long-Term Petroleum Contaminated Soil and Isolation of High-Efficiency Alkane-Degrading Strains Using an Improved Medium", World Journal of Microbiology and Biotechnology, 34(Art. 34):11P., Feb. 9, 2018.
English Summary Dated Dec. 22, 2023 of Notification of Office Action and Search Report Dated Dec. 8, 2023 From the National Intellectual Property Administration of the People's Republic of China Re. Application No. 202180032355.7. (9 Pages).
International Preliminary Report on Patentability Dated Oct. 13, 2022 From the International Bureau of WIPO Re. Application No. PCT/IL2021/050366. (10 Pages).

* cited by examiner

SEQUENCE LISTING

```
<160> NUMBER OF SEQ ID NOS: 4

<210> SEQ ID NO 1
<211> LENGTH: 775
<212> TYPE: DNA
<213> ORGANISM: Rhizobium capacia

<400> SEQUENCE: 1

gaacagtata ctgcccgacg gctaacattc atcgtttacg gcgtggacta ccagggtatc     60

taatcctgtt tgctccccac gctttcgcac ctcagcgtca gtaatggacc agtaagccgc    120

cttcgccact ggtgttcctc cgaatatcta cgaatttcac ctctacactc ggaattccac    180

ttacctcttc catactcaag atacccagta tcaaaggcag ttccgcagtt gagctgcggg    240

atttcacccc tgacttaaat atccgcctac gtgcgcttta cgcccagtaa ttccgaacaa    300

cgctagcccc cttcgtatta ccgcggctgc tggcacgaag ttagccgggg cttmttmtcc    360

gactaccgtc attatcttca tcggtgaaag agctttacaa ccctaaggcc ttcatcactc    420

acgcggcatg gctggatcag gcttgcgccc attgtccaat attccccact gctgcctccc    480

gtaggagtty gggccgtgtc tcagtcccaa tgtggctgat catmctctca gaccagctat    540

ggatcgtcgc cttggtaggc ctttacccca ccaactagct aatccaacgc gggccaatcc    600

ttccccgata aatctttccc ccgtagggcg tatgcggtat taattccagt ttcccggagc    660

tattccgcag gaaagggtat gttcccacgc gttactcacc cgtctgccac tccccttgcg    720

gggcgttcga cttgcatgtg ttaagcctgc cgccagcgtt cgttctgagc cataa         775


<210> SEQ ID NO 2
<211> LENGTH: 856
<212> TYPE: DNA
<213> ORGANISM: Escherichia coli

<400> SEQUENCE: 2
```

```
ttaacgcgtt agctccggaa gccacgcctc aagggcacaa cctccaagtc gacatcgttt     60

acggcgtgga ctaccagggt atctaatcct gtttgctccc cacgctttcg cacctgagcg    120

tcagtcttyg tccagggggc cgccttcgcc accggtattc ctccagatct ctacgcattt    180

caccgctaca cctggaattc taccccccctc tacragactc wagcytgcca gtatcaratg    240

cagttcccag gttgagcccg gggatttcac atcygactta acaaaccgcc tgcgtgcgct    300

ttacgcccag taattccgat taacgcttgc accctccgta ttaccgcggc tgctggcacg    360

gagttagccg gtgcttcttc tgcgggtaac gtcaatgagc aaaggtatta actttactmc    420

cttcctcccc gctgaaagta ctttacaacc cgaaggcctt cttcatacac gcggcatggc    480

tgcatcaggc ttgcgcccat tgtgcaatat tccccactgc tgcctcccgt aggagtctgg    540

accgtgtctc agttccagtg tggctggtca tcctctcaga ccagctaggg atcgtcgcct    600

aggtgagcct ttaccccacc tactagctaa tcccatctgg gcacatccga tggcaagagg    660

cccgaaggtc cccctctttg gtcttgcgac gttatgcggt attagctacc gtttccagta    720

gttatccccc tccatcaggc agtttcccag acattactca cccgtccgcc actcgtcagc    780

aaagcagcaa gctgcttyct gttaccgttc gacttgcatg tgttaggcct gccgccagcg    840

ttcaatctga gccata                                                    856
```

<210> SEQ ID NO 3
<211> LENGTH: 839
<212> TYPE: DNA
<213> ORGANISM: Pseudomonas

<400> SEQUENCE: 3

```
ccgatttaac gcgttagctc cggaagccac gcctcaaggg cacaacctcc aaatcgacat     60

cgtttacagc gtggactacc agggtatcta atcctgtttg ctccccacgc tttcgcacct    120

gagcgtcagt cttcgtccag ggggccgcct tcgccaccgg tattcctcca gatctctacg    180

catttcaccg ctacacctgg aattctaccc ccctctacga gactctagct tgccagtttc    240

aaatgcagtt cccaggttga gcccggggat ttcacatctg acttaacaaa ccgcctgcgt    300

gcgctttacg cccagtaatt ccgattaacg cttgcaccct ccgtattacc gcggctgctg    360

gcacggagtt agccggtgct tcttctgcga gtaacgtcaa ttgatgagcg tattaagctc    420

accaccttcc tcctcgctga aagtgcttta caacccgaag gccttcttca cacacgcggc    480

atggctgcat caggcttgcg cccattgtgc aatattcccc actgctgcct cccgtaggag    540

tctggaccgt gtctcagttc cagtgtggct ggtcatcctc tcagaccagc tagggatcgt    600

cgcctaggtg agccattacc ccacctacta gctaatccca tctgggcaca tctgatggca    660

agaggcccga aggtccccct ctttggtctt gcgacgttat gcggtattag ctaccgtttc    720

cagtagttat ccccctccat caggcagttt cccagacatt actcacccgt ccgccgctcg    780

tcacccaggg agcaagctcc cytgtgctac cgctcgactt gcatgtgtta agcctgccg     839
```

<210> SEQ ID NO 4
<211> LENGTH: 867
<212> TYPE: DNA
<213> ORGANISM: Serratia marcescens

<400> SEQUENCE: 4

```
gcgtctcccg gcggtcgmtt atcgcgttgc tgcgccacta agatctcaag gatcccaacg     60

gctagtcgac atcgtttacg gcgtggacta ccagggtatc taatcctgtt tgctccccac    120
```

-continued

| | |
|---|---|
| gctttcgcac ctcagtgtca gtatcagtcc aggtggtcgc cttcgccact ggtgttcctt | 180 |
| cctatatcta cgcatttcac cgctacacag gaaattccac caccctctac cgtactctag | 240 |
| ctcagtagtt ttggatgcag ttcccaggtt gagcccgggg atttcacatc caacttgctg | 300 |
| aaccacctac gcgcgcttta cgcccagtaa ttccgattaa cgcttgcacc cttcgtatta | 360 |
| ccgcggctgc tggcacgaag ttagccggtg cttattctgt tggtaacgtc aaaacagcaa | 420 |
| ggtattaact tactgccctt cctcccaact taaagtgctt tacaatccga agaccttctt | 480 |
| cacacacgcg gcatggctgg atcaggcttt cgcccattgt ccaatattcc ccactgctgc | 540 |
| ctcccgtagg agtctggacc gtgtctcagt tccagtgtga ctgatcatcc tctcagacca | 600 |
| gttacggatc gtcgccttgg taggccttta ccccaccaac tagctaatcc gacctaggct | 660 |
| catctgatag cgtgaggtcc gaagatcccc cactttctcc ctcaggacgt atgcggtatt | 720 |
| agcgcccgtt tccggacgtt atccccccac taccaggcag attcctaggc attactcacc | 780 |
| cgtcccgccg ctgaatccag gagcaagctc ccttcatccg ctcgacttgc atgtgtaggc | 840 |
| ctgcccgcca gcgttcaatc tgagcca | 867 |

BACTERIA FOR THE PREVENTION AND TREATMENT OF SMOKE-INDUCED LUNG DAMAGE

RELATED APPLICATIONS

This application is a National Phase of PCT Patent Application No. PCT/IL2021/050366 having International filing date of Mar. 31, 2021, which claims the benefit of priority under 35 USC § 119 (e) of U.S. Provisional Patent Application No. 63/002,611 filed on Mar. 31, 2020. The contents of which the above applications are all incorporated by reference as if fully set forth herein in their entirety.

SEQUENCE LISTING STATEMENT

The ASCII file, entitled 93888SequenceListing.txt, created on Sep. 27, 2022, comprising 5,081 bytes, submitted concurrently with the filing of this application is incorporated herein by reference.

FIELD AND BACKGROUND OF THE INVENTION

The present invention, in some embodiments thereof, relates to bacterial compositions for the preventing and treatment of smoke-induced lung damage and, more particularly, but not exclusively, to bacterial compositions capable of breaking down smoke residue in the respiratory system.

Smoke is a collection of airborne particulates and gases emitted when a material undergoes combustion or pyrolysis, together with the quantity of air that is entrained or otherwise mixed into the mass. Biomass burning smoke is commonly an unwanted by-product of fires, for example: tobacco cigarette smoke, cannabis cigarette smoke, bonfire smoke, stove smoke, wildfire smoke, fossil fueled power stations smoke, internal combustion engines smoke, vehicular emissions, tire fires smoke, open pits fire smoke, industrial smog, stubble burning smoke etc.

Tobacco is a product prepared from the leaves of the tobacco plant by curing them. The plant is part of the genus *Nicotiana* and of the Solanaceae (nightshade) family. While more than 70 species of tobacco are known, the chief commercial crop is *N. tabacum*. Dried tobacco leaves are mainly used for smoking in the form of cigarettes, cigars, pipe tobacco, flavored shisha tobacco, and Heated tobacco products (HTPs). They can also be consumed as snuff, chewing tobacco, dipping tobacco and snus.

The smoking of tobacco has been strongly linked, as a causative agent, to a number of respiratory diseases, mainly lung cancer and chronic obstructive pulmonary disease (COPD). In addition, it has been linked to non-respiratory diseases, such as heart disease and cancers of the upper digestive tract, including mouth, in addition to the urinary tract, the cervix and some types of leukemia. Smoking is one of the ten greatest contributors to global death and disease, with the WHO estimating that tobacco smoking causes 6 million deaths per year, 600,000 of them due to secondhand smoke. Tobacco is the greatest cause of preventable death, with half of smokers dying from related diseases or complications.

Tobacco smoke is a mixture of more than 5,000 chemicals, with at least 73 known carcinogens. This toxic and carcinogenic mixture is suggested to be the most significant source of toxic chemical exposure and chemically mediated disease in humans.

The most well-known and abundant chemical in tobacco smoke is nicotine—a stimulant and potent para-sympathomimetic alkaloid. It is one of the most commonly abused drugs and is highly addictive. Nicotine causes an increased risk of cardiovascular, respiratory, gastrointestinal disorders, in addition to decreased immune response and different types of cancer. An average cigarette yields about 2 mg of absorbed nicotine.

In a burning cigarette, the high temperatures in the combustion zone (800° C.-950° C.) result in a complete pyrolysis of tobacco. Immediately downstream there occurs a rapid drop in temperature (to 200° C.-600° C.) and a lack of oxygen contributing to incomplete combustion of the cigarette ingredients. As a result of these processes, a complex aerosol is generated and inhaled during smoking. This aerosol includes the particulate fraction, or tar, in liquid droplets suspended in a mixture of volatile and semi-volatile compounds and combustion gases (the gas fraction).

Smoking one cigarette exposes the human respiratory tract to between 15,000 and 40,000 μg of particulate matter (PM). The composition of cigarette smoke PM is comparable to that of other particles generated through an incomplete combustion of carbonaceous material, and includes—heterogeneous, amorphous and organic material such as burnt wood and coal.

Cigarette smoke can be defined as whole smoke (sometimes known as side-stream or side smoke) if it is not filtered. Breathing in other people's smoke is known as exposure to second-hand smoke or passive smoking. Second hand smoke is whole smoke. Whole smoke has a different chemical composition then directly inhaled, mainstream (firsthand) smoke, with evidence showing that whole smoke can have up to 6 times more particulates than mainstream smoke.

Tobacco tar is the common name for the resinous, partially combusted particulate matter produced by the burning of tobacco and other plant material in the act of smoking. Similar tar is produced from cannabis. Tar is toxic and damages the respiratory tract and upper gastrointestinal tract. It damages the smoker's lungs over time through various immunological, biochemical and mechanical processes. The tar is deposited on the ciliated epithelial cells throughout the respiratory tract, mainly in the trachea (windpipe) and in the alveoli (the small air bulbs in the lungs where carbon dioxide leaves the blood and oxygen enters it) of the lungs. Tar deposited in the lungs coats the cilia causing them to stop functioning and eventually die. This process contributes to the development of pathological conditions such as lung cancer and COPD, since the toxic particles in tobacco smoke are no longer impeded or trapped by the cilia but enter the alveoli directly. Tar damages also the mouth by rotting and blackening teeth, damaging gums, and desensitizing taste buds.

The majority of mutagenic and carcinogenic compounds present in tobacco smoke can be found in tar. Polycyclic aromatic hydrocarbons (PAHs), for example, are genotoxic and mutagenic because human tissues contain monooxygenases, which produce from the PAHs epoxides, that react with DNA causing mutations and cancer. The altered DNA sequences in genes that regulate cell replication can bring about malignant transformation of the cells. Low molecular weight PAHs, (with 2-4 rings) are potent carcinogens and can cause the initial stage of cancer development. Some bacteria have been shown to degrade PAHs via dioxygenases, which do not produce epoxides, therefore lowering the genotoxic potential of the PAHs.

Cannabis tar has been shown to contain similar chemicals as tobacco tar. The burning temperature of cannabis cigarette ("joint") is higher, leading to greater combustion. In addition, cannabis smokers tend to inhale more deeply and hold their breath longer than with cigarettes, so the tar accumulates in lower parts of the lungs too.

The hazards caused by smoking are a major motivation for many smokers worldwide to shift from smoking to use Heated (not burned) tobacco products (HTPs) and electronic-cigarettes. In HTPs, tobacco is heated to generate nicotine, which is the reason these products are highly addictive. There are various types of HTPs. HTPs generate smoke, gases, liquid and solid particles, including tar, which are inhaled by users. They also contain non-tobacco additives, and are often flavored. According to the WHO, currently, there is no evidence to demonstrate that HTPs are less harmful than conventional tobacco products. An electronic cigarette, also known as e-cigarette among other names, is an electronic device that simulates tobacco smoking. Electronic cigarettes are noncombustible tobacco products. Using an e-cigarette is called "vaping". E-cigarettes work by heating a liquid, which vaporizes and may or may not contain nicotine and in most cases does not contain tobacco. E cigarettes are claimed to be substantially safer than tobacco cigarettes, since there is no ash, or carbon monoxide entering inhaler's lungs. However, the safety of electronic cigarettes is questioned lately. Trials in animals, tissue culture and humans have been published in the last few years demonstrating the dangers of e-cigarettes. The hazardous effects include increase in oxidative stress and inflammation, infections, airway remodeling and initiating changes in lung tissue that could lead to COPD.

The serious problem of residues caused by tobacco and cannabis smoke accumulating mainly in the respiratory system, but also in other tissues of the human body, has not been solved up to this day. There exists a long-felt need for treatment and prevention of the pathological effects of these deleterious pollutants.

Background art includes Van de Wiele et al., Environmental Health perspectives, Volume 113, Number 1, January 2005; Ruan and Min., Journal of Environmental Science and Health, 40:2073-2083, 2005; U.S. Patent Application No. 20210069269; Le Noci et al., 2018, Cell Reports 24, 3528-3538; and Evsyutina Y, et al., World J Respirol 2017; 7(2): 39-47 [DOI: 10.5320/wjr.v7.i2.39]

SUMMARY OF THE INVENTION

According to an aspect of the present invention there is provided a method of treating or preventing a disease associated with smoke residue in a subject or alleviating the symptoms caused by withdrawal from the use of nicotine, the method comprising administering to the subject a therapeutically effective amount of at least one agent which increases the amount of bacteria which are capable of breaking down the smoke residue in the subject, thereby treating of preventing the disease associated with smoke residue or alleviating the symptoms caused by withdrawal from the use of nicotine.

According to an aspect of the present invention there is provided an agent which increases the amount of bacteria which are capable of breaking down the smoke residue in a subject, for use in treating of preventing a disease associated with smoke residue or alleviating the symptoms caused by withdrawal from the use of nicotine.

According to an aspect of the present invention there is provided a pharmaceutical composition comprising at least one species of bacteria which are capable of breaking down smoke residue in the lungs or mouth of a subject, the composition being formulated for oral or pulmonary delivery.

According to an aspect of the present invention there is provided a device for delivering bacteria to the lungs, wherein the bacteria comprise at least one species of bacteria which is capable of breaking down smoke residue in the lungs of a subject.

According to an aspect of the present invention there is provided a method of enriching for a bacteria which is useful for breaking down smoke residue in the respiratory system of a subject comprising culturing bacteria of the lung microbiome of a subject on a medium which comprises smoke residue under conditions that allow for propagation of bacteria which degrade smoke residue, thereby enriching for the bacteria.

According to embodiments of the present invention, the smoke residue on the fingers or in the respiratory system of the subject.

According to embodiments of the present invention, the smoke residue is in the respiratory system of the subject.

According to embodiments of the present invention, the smoke residue is in the lungs of the subject.

According to embodiments of the present invention, the smoke residue is generated from tobacco smoking, marijuana smoking, environmental smoke, bonfire smoke, forest-fire smoke, airpit smoke, stove heater smoke, vehicle emission and air pollution.

According to embodiments of the present invention, the method is for preventing a disease associated with smoke residue and the subject does not have a lung disease.

According to embodiments of the present invention, the subject smokes more than 1 cigarette a day.

According to embodiments of the present invention, the method is for preventing a disease associated with smoke residue and the subject is not diagnosed with cancer.

According to embodiments of the present invention, the subject is healthy.

According to embodiments of the present invention, the subject is a non-smoker.

According to embodiments of the present invention, the cigarette comprises tobacco or marijuana.

According to embodiments of the present invention, the agent is the bacteria.

According to embodiments of the present invention, the bacteria are genetically modified to express a protein that increases the degradation of smoke residue in the lungs.

According to embodiments of the present invention, the bacteria are non-genetically modified.

According to embodiments of the present invention, the agent is a prebiotic.

According to embodiments of the present invention, the agent comprises bacteria which are enriched in the lung microbiome or gut microbiome of a healthy smoker as compared to a healthy non-smoker.

According to embodiments of the present invention, the bacteria are of a species selected from the group consisting of *Rhizobium pusense, E. coli, Serratia marcescens* and *Pseudomonas aeruginosa.*

According to embodiments of the present invention, the bacteria are of a species selected from the group consisting of *Rhizobium pusense, E. coli* and *Serratia marcescens*

According to embodiments of the present invention, the at least one agent is administered orally or by inhalation.

According to embodiments of the present invention, the at least one agent is administered using a Dry-powder inhaler (DPI), a Metered-dose inhaler, a nebulizer or a vaporizer.

According to embodiments of the present invention, the pharmaceutical composition is for use in treating or preventing a condition or disease associated with smoke residue or for alleviating the symptoms caused by withdrawal from the use of nicotine.

According to embodiments of the present invention, the smoke residue comprises cigarette smoke residue.

According to embodiments of the present invention, the at least one species of bacteria is enriched in the lung microbiome or gut microbiome of a healthy smoker as compared to a healthy non-smoker.

According to embodiments of the present invention, the at least one species of bacteria is selected from the group consisting of *Rhizobium pusense, E. coli, Pseudomonas aeruginosa* and *Serratia marcescens.*

According to embodiments of the present invention, the at least one species is selected from the group consisting of *Rhizobium pusense, E. coli* and *Serratia marcescens.*

According to embodiments of the present invention, the bacteria are genetically modified to express a protein that increases the degradation of smoke residue in the lungs.

According to embodiments of the present invention, the bacteria are non-genetically modified.

According to embodiments of the present invention, the pharmaceutical composition is formulated as a liquid or a solid.

According to embodiments of the present invention, the pharmaceutical composition is formulated as an aerosol, a spray, a liquid or a vapor.

According to embodiments of the present invention, the pharmaceutical composition is comprised in a chewing gum, a mouth rinse, a lung wash, a lollypop, an oral spray or an orally disintegrating tablet.

According to embodiments of the present invention, the disease associated with smoke residue is selected from the group consisting of lung cancer, oral cancer or COPD.

According to embodiments of the present invention, the at least one species of bacteria is enriched in the lung microbiome or gut microbiome of a healthy smoker as compared to a healthy non-smoker.

According to embodiments of the present invention, the at least one species is selected from the group consisting of *Rhizobium pusense, E. coli, Pseudomonas aeruginosa* and *Serratia marcescens.*

According to embodiments of the present invention, the at least one species is selected from the group consisting of *Rhizobium pusense, E. coli* and *Serratia marcescens.*

According to embodiments of the present invention, the device is selected from the group consisting of a Dry-powder inhaler (DPI), a Metered-dose inhaler, a nebulizer and a vaporizer.

According to embodiments of the present invention, the subject is a cigarette smoker.

According to embodiments of the present invention, the smoke residue is cigarette smoke residue.

According to embodiments of the present invention, the method further comprises isolating the bacteria following the enriching.

According to embodiments of the present invention, the method further comprises sequencing the bacteria following the enriching.

According to an aspect of the present invention there is provided a composition for the treatment of tar, comprising a therapeutic dose of at least one type of bacteria, wherein the bacteria is capable of at least partial degradation of tar.

According to embodiments of the present invention, the tar is deposited in the mouth or the respiratory system.

According to embodiments of the present invention, the tar is deposited by the inhaling of smoke, the smoke generated by the combustion or partial combustion of an organic material.

According to embodiments of the present invention, the organic material is selected from a group consisting of tobacco and cannabis.

According to embodiments of the present invention, the bacteria degrades tar by bio-deterioration, bio-fragmentation or assimilation.

According to embodiments of the present invention, the composition is formulated as a liquid or a solid.

According to embodiments of the present invention, the formulation is administered as a solid, an aerosol, a spray, a liquid or a vapor.

According to embodiments of the present invention, the formulation is administered by a Dry-powder inhaler (DPI), a Metered-dose inhaler, a nebulizer, a vaporizer, chewing gum, mouth rinse.

According to embodiments of the present invention, the formulation is administered as a lung wash.

According to embodiments of the present invention, the formulation is administered as a mouthwash, a lollypop, an oral spray, an orally disintegrating tablet or chewing gum.

According to embodiments of the present invention, the formulation additionally comprises adhesives, stabilizers, emulsifiers, detergents, nutrients, salts, food additives, taste additives.

According to embodiments of the present invention, the degradation effects the quantity, chemical content, particle size, viscosity, hardness, adhesiveness, surface and color, of the tar.

According to an aspect of the present invention there is provided a method of degrading tar, comprising steps of:

a. providing a therapeutic dose of a bacteria capable of degrading tar; and
b. administering the bacteria to subjects.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
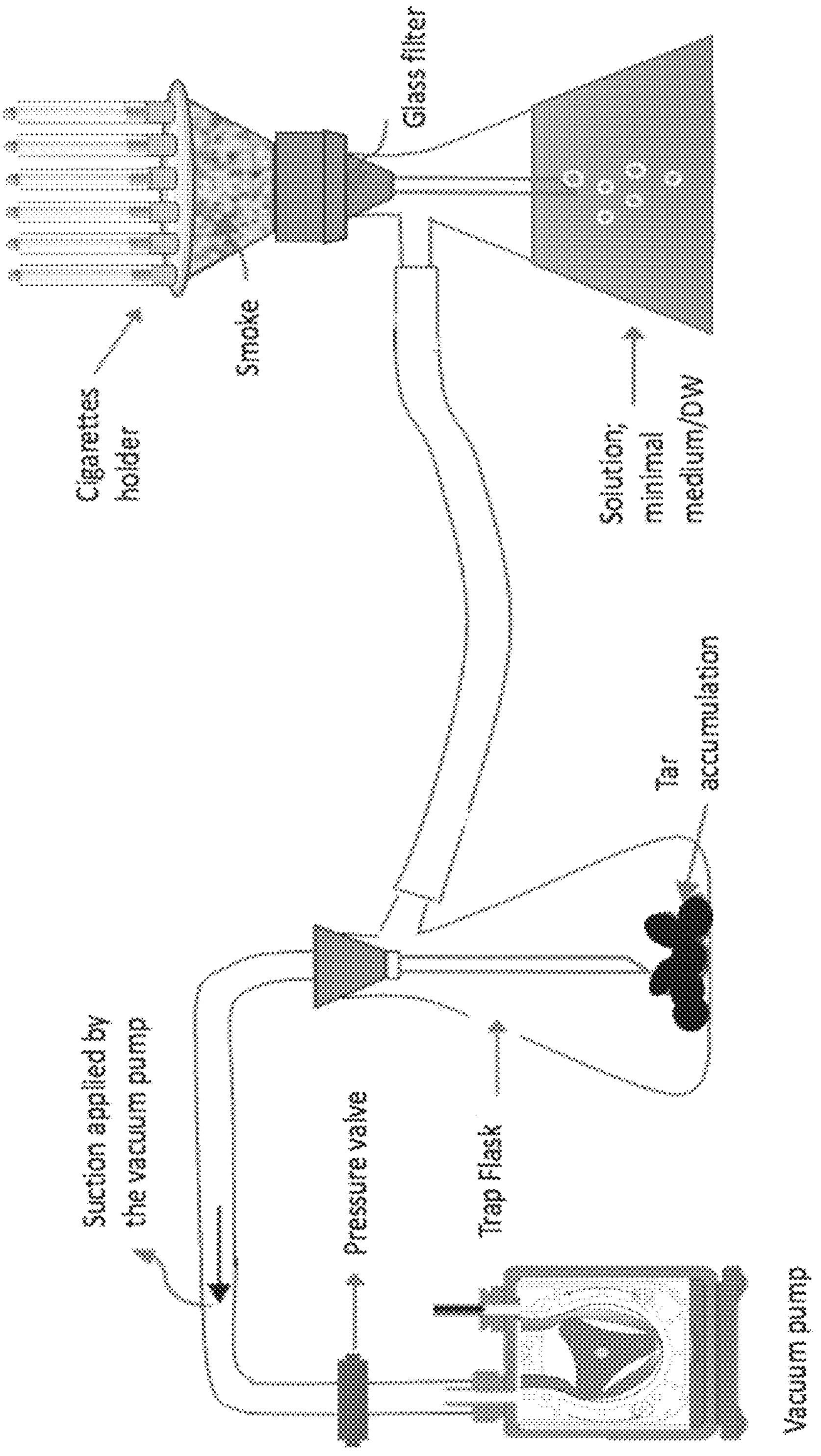
FIG. 1 is a Schematic illustration of the smoking system which can be used to collect smoke extract to be used for identifying bacteria which are capable of breaking down tobacco smoke residue components.

The present invention, in some embodiments thereof, relates to bacterial compositions for the preventing and treatment of smoke-induced lung damage and, more particularly, but not exclusively, to bacterial compositions capable of breaking down smoke residue in the respiratory system.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The respiratory system extends from the nose and mouth and upper airway to the alveolar surface of the lungs, where gas exchange occurs. Inhaled tobacco smoke moves from the mouth through the upper airway, ultimately reaching the alveoli. As the smoke moves more deeply into the respiratory tract, more soluble gases are adsorbed and particles are deposited in the airways and alveoli. The substantial doses of carcinogens and toxins delivered to these sites place smokers at risk for malignant and nonmalignant diseases involving all components of the respiratory tract including the mouth.

At present, there is no treatment for the condition of tar-contaminated lungs.

Based on the successful use of oil-degrading microorganisms for the environmental cleanup of oil-contaminated soil ecosystems, the present inventors now suggest use of tar-degrading microorganisms to clean human tar-contaminated respiratory ecosystems.

Since hydrocarbon-degrading bacteria exist in environments rich in hydrocarbons, such as areas with oil pollution (Rosenberg, E. 2006. Hydrocarbon-oxidizing bacteria. In: The Prokaryotes. Eds. M. Dworkin, S. Falkow, E. Rosenberg, K. H. Schleifer, and E. Stackebrandt. Springer, New York. Vol. 2, p. 564-577; Xu X., Liu W., Tian S. et al. 2018. Front Microbiol), and in tobacco tar-contaminated soil (Ruan A and Min H. 2005. Studies on Microbiological degradation of tobacco tar. J Environ Sci Health 40:2073-2083), the present inventors contemplated that similar tar-degrading bacteria should also exist in the respiratory systems of smokers.

Therefore, in order to identify bacterial candidates capable of breaking down smoke residue in the lungs, the present inventors sought tar-degrading bacteria in the lung microbiome of healthy smokers. Using an enrichment culture containing smoke residues as the sole carbon and energy sources (see FIG. 1), the present inventors isolated 4 different bacteria from the lung microbiome, and showed that these bacteria were capable of degrading a wide variety of toxic compounds present in smoke residue (FIGS. 2A-4B).

The present inventors expect that the isolated bacteria, and agents which increase the level of these bacteria in the lungs (e.g. prebiotic agents etc.) should reduce the risks of lung cancer, COPD and of other adverse health effects and be effective as therapeutics as well.

Since the bacteria were shown to also decrease the level of nicotine in vitro, the present inventors propose that the bacteria can also serve as alleviating the symptoms caused by withdrawal from the use of nicotine agents and prevent diseases caused by nicotine.

Thus, according to a first aspect of the present invention, there is provided a method of treating or preventing a disease associated with smoke residue in the subject or alleviating the symptoms caused by withdrawal from the use of nicotine, the method comprising administering to a subject a therapeutically effective amount of at least one agent which increases the amount of bacteria which are capable of breaking down the smoke residue in the subject, thereby treating of preventing the disease associated with smoke residue or alleviating the symptoms caused by withdrawal from the use of nicotine.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition.

The term "preventing" as used herein includes preventing the appearance of clinical or aesthetical symptoms of a condition.

The term "smoke residue" as used herein, refers to the resinous, partially combusted particulate matter produced by the burning of material (such as tobacco and cannabis in the act of smoking), which in one embodiment may be deposited as tar along the respiratory tract and mouth.

The smoke residue (e.g. tar deposits) may be in the respiratory system (e.g. lungs) of the subject, in the oral cavity of the subject (e.g. on the teeth) or may be on the skin of the subject. In one embodiment, components of the smoke residue are in the internal organs of the subject.

The smoke residue may be as a result of any type of smoke including but not limited to tobacco smoking, marijuana smoking, environmental smoke, wildfire smoke, stove smoke, fossil fueled power stations smoke, internal combustion engines smoke, vehicular emissions, tire fires, open burn pits smoke, industrial smog, stubble burning etc.

The ability to break down (i.e. bio remediate) smoke residue may include the ability to break down at least one, at least two at least three, at least four, at least five of the following smoke residue components: Alkaloids such as nicotine and nicotyrine; N-Nitrosamines; Polycyclic aromatic hydrocarbons (PAHs); Aromatic amines; Heterocyclic aromatic amines such as pyridine; and Alkanes such as tetradecane; Additional compounds are also included such as: 2-pyrrollidinone, 5-methyltricyclo, Z-butylidinephthalide.

Diseases associated with smoke residue or nicotine include, but are not limited to different types of cancer, chronic bronchitis, Chronic Obstructive Pulmonary Disease (COPD), emphysema, pulmonary hypertension, bacterial and viral pneumonia, cardiovascular diseases and reproductive and developmental effects.

Examples of cancers that can be treated/prevented include, but are not limited to cancers of the respiratory tract including for example throat, larynx, trachea, bronchioles, lung.

Other contemplated cancers include kidney cancer, pelvic cancer, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; triple negative breast cancer, Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; osteocarcinoma, ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

In a particular embodiment, the cancer that is treated/prevented is lung cancer or oral cancer.

Subjects which can be treated for such diseases include mammalian subjects, preferably human subjects.

In one embodiment, the subject which is treated has been pre-diagnosed with the disease.

In one embodiment, the subject that is treated is a smoker (e.g. smoke at least 1, 2, 3, 4, 5, 6, 7, 8, 9, or 10 cigarettes a day).

In still another embodiment, the subject that is treated does not have cystic fibrosis.

In another embodiment, the subject that is treated is a non-smoker.

The term "non-smoker" refers to a subject that doesn't smoke more than 1 cigarette a week.

According to a particular embodiment, the subject that is treated has a lung disease (e.g. COPD) and is not suffering from cancer.

According to another embodiment, the subject that is treated has cancer and is not suffering from a lung disease (e.g. COPD, cystic fibrosis).

When the subject is administered the agent as a preventative measure, the subject may be healthy, suffering from a non-lung related disease, a smoker or a non-smoker.

As mentioned, the present inventors propose administration of agents which increase the amount and/or activity of at least one species of bacteria capable of breaking down smoke residue in the subject.

Preferably, the contemplated agents are capable of increasing the amount of bacteria capable of breaking down smoke residue in the lungs and/or mouth of the subject.

In one embodiment, the agent comprises a prebiotic which enhances the activity and/or amount of the tar-degrading bacteria.

In another embodiment, the agent comprises the bacteria itself which is capable of breaking down the tar.

The agent may be a single bacterial species or comprise a plurality of bacterial species (e.g. 2, 3, 4, 5, 6, 7, 8, 9, 10 or more). Preferably, the agent does not comprise more than 50 bacterial species, more than 40 bacterial species, more than 30 bacterial species, more than 20 bacterial species or even more than 10 bacterial species.

According to a particular embodiment, the bacteria are present in the lung microbiome or gut microbiome of a healthy smoker.

In another embodiment, the bacteria are isolated from the lung microbiome or gut microbiome of a healthy smoker.

The term "isolated" or "enriched" encompasses bacteria that have been (1) separated from at least some of the components with which it was associated when initially produced (whether in nature or in an experimental setting), and/or (2) produced, prepared, purified, and/or manufactured by the hand of man. Isolated microbes may be separated from at least about 10%, about 20%, about 30%, about 40%, about 50%, about 60%, about 70%, about 80%, about 90%, or more of the other components with which they were initially associated. In some embodiments, isolated microbes are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a microbe or other material that has been separated from at least some of the components with which it was associated either when initially produced or generated (e.g., whether in nature or in an experimental setting), or during any time after its initial production. A microbe or a microbial population may be considered purified if it is isolated at or after production, such as from a material or environment containing the microbe or microbial population, and a purified microbe or microbial population may contain other materials up to about 10%, about 20%, about 30%, about 40%, about 50%, about 60%, about 70%, about 80%, about 90%, or above about 90% and still be considered "isolated." In some embodiments, purified microbes or microbial population are more than about 80%, about 85%, about 90%, about 91%, about 92%, about 93%, about 94%, about 95%, about 96%, about 97%, about 98%, about 99%, or more than about 99% pure. In the instance of microbial compositions provided herein, the one or more microbial types present in the composition can be independently purified from one or more other microbes produced and/or present in the material or environment containing the microbial type. Microbial compositions and the microbial components thereof are generally purified from residual habitat products.

In certain embodiments, at least 50%, 55%, 60%, 65%, 70%, 75%, 80%, 85%, 90%, 95%, 96%, 97%, 98%, 99% of the bacteria are capable of degrading smoke residue which has been deposited in the body of the subject.

In another embodiment, the bacteria are enriched (e.g. by more than 2 fold, 3 fold, 4 fold, 5 fold, 10 fold or even 20 fold) in the lung microbiome of a healthy smoker as compared to a healthy non-smoker.

As used herein, the term "microbiome" refers to the aggregate of microorganisms that resides on or within any of a number of human organs and some bio-fluids, including the lung, skin, mammary glands, seminal fluid, vagina, uterus, saliva, oral mucosa, conjunctiva, biliary and gastrointestinal tracts. The human microbiota includes bacteria, archaea, fungi, protists and viruses.

The phrase "lung microbiome" refers to the pulmonary microbial community found in the respiratory tract particularly on the mucous layer and epithelial surfaces. Particular bacterial genii known to exist in the lung microbiome include *Prevotella, Sphingomonas, Pseudomonas, Acinet obacter, Fusobacterium, Megasphaera, Veillonella, Staphylococcus* and *Streptococcus.*

In one embodiment, the bacteria are of a species selected from the group consisting of *Rhizobium pusense* (e.g. having a 16S rRNA gene sequence as set forth in SEQ ID NO: 1), *E. coli* (e.g. having a 16S rRNA gene sequence as set forth in SEQ ID NO: 2), *Pseudomonas aeruginosa* (e.g. having a 16S rRNA gene sequence as set forth in SEQ ID NO: 3) and *Serratia marcescens* (e.g. having a 16S rRNA gene sequence as set forth in SEQ ID NO: 4).

According to a specific embodiment, the genome of the bacteria comprise a 16S rRNA sequence at least 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9%, 99.95% identical to any one of the sequences as set forth in SEQ ID NOs: 1-4.

As used herein, "percent homology", "percent identity", "sequence identity" or "identity" or grammatical equivalents as used herein in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89(22): 10915-9].

Percent identity can be determined using any homology comparison software, including for example, the BlastN software of the National Center of Biotechnology Information (NCBI) such as by using default parameters.

Other exemplary sequence alignment programs that may be used to determine % homology or identity between two sequences include, but are not limited to, the FASTA package (including rigorous (SSEARCH, LALIGN, GGSEARCH and GLSEARCH) and heuristic (FASTA, FASTX/Y, TFASTX/Y and FASTS/M/F) algorithms, the EMBOSS package (Needle, stretcher, water and matcher), the BLAST programs (including, but not limited to BLASTN, BLASTX, TBLASTX, BLASTP, TBLASTN), megablast and BLAT. In some embodiments, the sequence alignment program is BLASTN. For example, 95% homology refers to 95% sequence identity determined by BLASTN, by combining all non-overlapping alignment segments (BLAST HSPs), summing their numbers of identical matches and dividing this sum with the length of the shorter sequence.

In some embodiments, the sequence alignment program is a basic local alignment program, e.g., BLAST. In some embodiments, the sequence alignment program is a pairwise global alignment program. In some embodiments, the pairwise global alignment program is used for protein-protein alignments. In some embodiments, the pairwise global alignment program is Needle. In some embodiments, the sequence alignment program is a multiple alignment program. In some embodiments, the multiple alignment program is MAFFT. In some embodiments, the sequence alignment program is a whole genome alignment program. In some embodiments, the whole genome alignment is performed using BLASTN. In some embodiments, BLASTN is utilized without any changes to the default parameters.

According to some embodiments of the invention, the identity is a global identity, i.e., an identity over the entire nucleic acid sequences of the invention and not over portions thereof.

In another embodiment, the bacteria are of a species selected from the group consisting of *Rhizobium pusense, E. coli* and *Serratia marcescens.*

The present inventors contemplated administering a single strain of bacteria belonging to *Rhizobium pusense, E.*

*coli* and/or *Serratia marcescens* species, no more than two strains of bacteria belonging to *Rhizobium pusense, E. coli* and/or *Serratia marcescens* species, no more than three strains of bacteria belonging to *Rhizobium pusense, E. coli* and/or *Serratia marcescens* species, no more than four strains of bacteria belonging to *Rhizobium pusense, E. coli* and/or *Serratia marcescens* species, no more than five strains of bacteria belonging to *Rhizobium pusense, E. coli* and/or *Serratia marcescens* species, no more than ten strains of bacteria belonging to *Rhizobium pusense, E. coli* and/or *Serratia marcescens* species.

Identification of additional bacteria capable of degrading smoke-induced residue can be carried out by culturing bacteria of the lung microbiome on a medium which comprises cigarette smoke residues under conditions that allow for propagation of bacteria which degrade cigarette smoke residues.

In one embodiment, the bacteria is derived from a respiratory system (e.g. lung) microbiome of a cigarette smoker.

Samples of lung microbiome may be obtained using an invasive procedure (e.g. Bronchoalveolar lavage, using bronchoscopic protected brushes, or excised lung tissue) or an invasive procedure (e.g. sputum or tracheal aspirate).

The bacteria can be isolated from such a system and cultured as a single isolate. The bacteria can then be characterized (e.g. sequenced).

The bacteria present in the therapeutic composition are typically viable (e.g. capable of propagating when cultured in the appropriate medium, or inside the body, following administration).

In still another embodiment, the bacteria are attenuated such that they are not capable of causing disease.

The bacteria described herein may be genetically modified to enhance their ability to break down the smoke residues in the subject.

For example, in some embodiments, the bacterium comprises a nucleic acid encoding an enzyme known to be involved in smoke residue degradation (e.g. the genes encoding the degradation pathway of an aliphatic hydrocarbon such as hexadecane from a *Pseudomonas* sp. hexadecane hydroxylase, alcohol dehydrogenase and aldehyde dehydrogenase. Another example, the first genes encoding the degradation of benzene also from *Pseudomonas* sp. benzene dioxygenase and catechol dioxygenase.) operably linked to transcriptional regulatory elements, such as a bacterial promotor. The transcriptional regulatory element can further comprise a secretion signal. In some embodiments, the enzyme known to be involved in smoke residue degradation is constitutively expressed by the bacterium. In some embodiments, the enzyme known to be involved in smoke residue degradation is inducibly expressed by the bacterium (e.g., it is expressed upon exposure to a sugar or an environmental stimulus like low pH or an anaerobic environment). In some embodiments, the bacterium comprises a plurality of nucleic acid sequences that encode for multiple different enzymes known to be involved in smoke residue degradation that can be expressed by the same bacterial cell.

Examples of bacterial promoters include but are not limited to STM1787 promoter, pepT promoter, pflE promoter, ansB promoter, vhb promoter, FF+20* promoter or p(luxI) promoter.

In another embodiment, the bacteria are not genetically modified.

Methods for producing bacteria may include three main processing steps. The steps are: organism banking, organism production, and preservation.

For banking, the strains included in the bacteria may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. Another examples would be a medium composed of 10 g/L beef extract, 10 g/L peptone, 5 g/L sodium chloride, 5 g/L dextrose, 3 g/L yeast extract, 3 g/L sodium acetate, 1 g/L soluble starch, and 0.5 g/L L-cysteine HCl, at pH 6.8. A variety of microbiological media and variations are well known in the art (e.g., R. M. Atlas, Handbook of Microbiological Media (2010) CRC Press).

The medium may also comprise smoke residue compounds including for example polycyclic aromatic hydrocarbons (PAHs) and/or nicotine. Culture media can be added to the culture at the start, may be added during the culture, or may be intermittently/continuously flowed through the culture. The isolated strains in the microbial composition may be cultivated alone, as a subset of the microbial composition, or as an entire collection comprising the microbial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For microbial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions, an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine-HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term microbial composition storage stability at temperatures elevated above cryogenic. If the microbial composition comprises, for example, spore forming species and results in the production of spores, the final composition may be purified by additional means such as density gradient centrifugation preserved using the techniques described above.

Microbial composition banking may be done by culturing and preserving the strains individually, or by mixing the strains together to create a combined bank. As an example of cryopreservation, a microbial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Microbial production may be conducted using similar culture steps to banking, including medium composition and culture conditions. It may be conducted at larger scales of operation, especially for clinical development or commercial production. At larger scales, there may be several subcultivations of the microbial composition prior to the final cultivation. At the end of cultivation, the culture is harvested to enable further formulation into a dosage form for administration. This can involve concentration, removal of undesirable medium components, and/or introduction into a chemical milieu that preserves the microbial composition and renders it acceptable for administration via the chosen route. After drying, the powder may be blended to an appropriate potency, and mixed with other cultures and/or a filler such as microcrystalline cellulose for consistency and ease of handling, and the bacterial composition formulated as provided herein.

Since the present inventors uncovered bacteria that were capable of degrading nicotine, the present inventors also contemplate administering the bacteria in order to alleviate or reduce the symptoms caused by withdrawal from the use of nicotine.

For preventing or reducing symptoms caused by withdrawal from the use of nicotine, in one embodiment, the bacteria are not of the *Lactobacillus* species, *Bifidobacterium* species or *L. rhamnosus* species.

In another embodiment, for the prevention or reduction of symptoms caused by withdrawal from the use of nicotine, the bacteria are not of the below listed species—*L. acidophilus, L. brevis, L. bulgaricus, L. casei, L. crispatus, L. delbrueckii, L. fermentum, L. gasseri, L. helveticus, L. lactis, L. plantarum, L. reuteri, L. rhamnosus, L. salivarius* or *L. paracasei.*

Common symptoms in subjects experiencing tobacco or nicotine withdrawal include, for example, depression, irritability, anxiety, restlessness, hunger, lack of concentration, insomnia, nervous tremor, light-headedness, and the craving for tobacco or nicotine. In addition to the difficulty related to cessation of smoking, common side effect that subjects experience when attempting to quit smoking is a substantial increase in appetite because they are craving food as a response to their anxiety. This increased hunger results in undesirable increases in body weight.

By alleviating symptoms caused by withdrawal of the use of nicotine, the present inventors contemplate using the bacterial compositions for encouraging (i.e. promoting) smoking cessation, or reduction of the amount of tobacco smoking.

The bacteria can be provided per se or may be formulated in a pharmaceutical composition.

As used herein a "pharmaceutical composition" refers to a preparation of one or more of the active ingredients described herein with other chemical or biological components such as physiologically suitable carriers and excipients. The purpose of a pharmaceutical composition is to facilitate administration of a compound to an organism.

Herein the term "active ingredient" refers to the bacteria accountable for the biological effect.

Hereinafter, the phrases "physiologically acceptable carrier" and "pharmaceutically acceptable carrier" which may be interchangeably used refer to a carrier or a diluent that does not abrogate the biological activity and properties of the administered compound.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intrapulmonary or intraocular injections.

Alternately, one may administer the pharmaceutical composition in a local rather than systemic manner, for example, via inhalation into the lungs of the subject. For example, the bacteria may be comprised in a cigarette or an e-cigarette. The cigarette may or may not comprise nicotine.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

The active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

Particular formulations suitable for oral administration include a chewing gum, a mouth rinse, a lung wash, a lollypop, an oral spray or an orally disintegrating tablet.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

According to a particular embodiment, the bacteria are administered using a Dry-powder inhaler (DPI), a Metered-dose inhaler, a nebulizer or a vaporizer.

The compositions may be suspensions, solutions or emulsions in oily or aqueous vehicles, and may contain formulatory agents such as suspending, stabilizing and/or dispersing agents.

Pharmaceutical compositions include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (bacteria) effective to prevent, or slow down the development of the disorder (e.g., lung cancer) or prolong the survival of the subject being treated (e.g. COPD).

According to an embodiment of the present invention, an effective amount of the bacteria of some embodiments of the present invention is an amount selected to neutralize or reduce lung-damaging smoke components present in the lung cells of the subject.

The bacterial composition may be in a powdered dry form. In addition, the bacteria may have undergone processing in order for it to increase its survival. For example, the microorganism may be coated or encapsulated in a polysaccharide, fat, starch, protein or in a sugar matrix. Standard encapsulation techniques known in the art can be used. For example, techniques discussed in U.S. Pat. No. 6,190,591, which is hereby incorporated by reference in its entirety, may be used.

According to a particular embodiment, the bacteria are formulated in a food product, functional food or nutraceutical.

In some embodiments, a food product, functional food or nutraceutical is or comprises a dairy product. In some embodiments, a dairy product is or comprises a yogurt product. In some embodiments, a dairy product is or comprises a milk product.

In some embodiments, a dairy product is or comprises a cheese product. In some embodiments, a food product, functional food or nutraceutical is or comprises a juice or other product derived from fruit. In some embodiments, a food product, functional food or nutraceutical is or comprises a product derived from vegetables. In some embodiments, a food product, functional food or nutraceutical is or comprises a grain product, including but not limited to cereal, crackers, bread, and/or oatmeal. In some embodiments, a food product, functional food or nutraceutical is or comprises a rice product. In some embodiments, a food product, functional food or nutraceutical is or comprises a meat product.

In certain embodiments, the pharmaceutical composition comprises at least $1\times10^3$ colony forming units (CFUs), $1\times10^4$ colony forming units (CFUs), $1\times10^5$ colony forming units (CFUs), $1\times10^6$ colony forming units (CFUs), $1\times10^7$ colony forming units (CFUs), $1\times10^8$ colony forming units (CFUs), $1\times10^9$ colony forming units (CFUs), $1\times10^{10}$ colony forming units (CFUs) of bacteria capable of degrading at least one harmful component of smoke.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays may be used to determine disappearance of break-down products.

Depending on the severity and responsiveness of the condition to be treated, dosing can be of a single or a plurality of administrations, with course of treatment lasting from several days to several weeks or until cure is effected or diminution of the disease state is achieved. For prevention, the course of treatment may be months or years.

The amount of a composition to be administered will, of course, be dependent on the subject being treated, the severity of the affliction, the manner of administration, the judgment of the prescribing physician, etc.

Prior to administration, the subject may be pretreated with an agent which reduces the number of naturally occurring microbes in the lung or gut microbiome (e.g. by antibiotic treatment). According to a particular embodiment, the treatment significantly eliminates the naturally occurring lung microbiota by at least 20%, 30% 40%, 50%, 60%, 70%, 80% or even 90%.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It is expected that during the life of a patent maturing from this application many relevant smoke residue degrading bacteria will be discovered and the scope of the term smoke residue degrading bacteria are intended to include all such bacteria a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Selection and Characterization of Smoke Residue Degrading Bacteria Minimal media containing smoke residues (MMS) was formulated to mimic the smoke components deposited in the lungs. An artificial smoking system was developed that mimics active smoking which "inhales" cigarette smoke through glass microfiber filters (FIG. 1). An enrichment culture procedure was then carried out, by incubating the mucus of heavy smokers in MMS at 37° C. for four days. This procedure was repeated three times, to yield bacteria that multiplied on specific cigarette smoke extract ingredients. The pure cultures were grown on MMS media to confirm that each isolate was a smoke residue degrading bacterium. 16S rRNA gene sequences were aligned with the best matched relative sequences in the GenBank database, using the basic alignment nucleotide search tool (BLAST) at the National Center for Biotechnology Information (NCBI) database.

Results

Three isolates were clustered with the reference sequences from NCBI, indicating a high alignment of above 99% similarity (Table 1). The most prominent bacterial isolates, Yug, Mas and M-1, which are gram negative, were identified as *Rhizobium pusense, E. coli* and *Serratia marcescens*, respectively. The growth profiles of all of the isolates were monitored over six days by measuring both the $OD_{600}$ and the viable counts. The absorbance kinetics were used to calculate growth rates in the log-stage (Table 1). Additionally, no antagonistic effects were observed in cross-growth relationship testing done by seeding each isolate against the other on agar plates.

TABLE 1

| Smoke residue degrading isolate | Best match isolate (Accession No.) | % similarity | Doubling time $t_D$ [h] | Cross growth inhibition effect |
|---|---|---|---|---|
| Yug | *Rhizbium pusense* (MN092364.1) | 99% | 2.9 | none |
| Mas | *Escherichia coli* (MH196345.1) | 99% | 2.15 | none |
| M-1 | *Serratia marcescens* (MN853572.1) | 99% | 3 | none |

GC-MS analyses were performed on the MMS medium before and after the growth of each isolate and of a mixture of the isolates. In addition, pure compounds were used as standards in the analysis, in order to determine how much of each carbon compound in the medium was degraded by the bacteria. The standards were selected based on the degraded components of the tar extract, either by each isolate that was grown separately or the mixture of all.

Figure 2A:
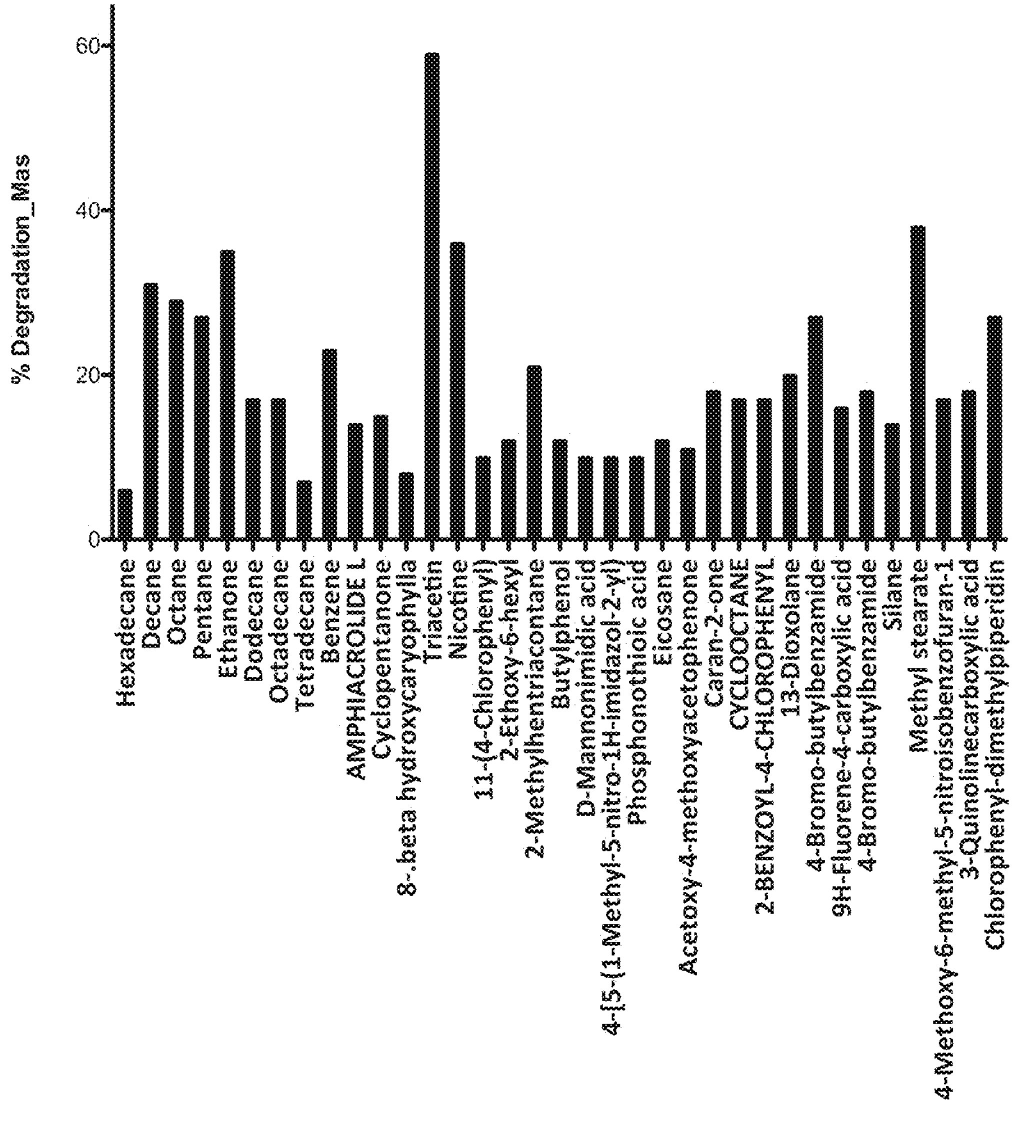
FIGS. 2A-C are bar graphs illustrating degradation of smoke residue components by the isolated bacteria: GC-MS analysis of Mas (A), M-1 (B) and Yug (C). Percent degradation was calculated by comparing the absolute area values of the GC-MS chart of the controls to those of the specific cultures. The columns represent percent degradation of the different compounds after five days of growth at 37° C., relative to minimal media containing smoke residues (MMS) alone incubated with no bacteria.
Figure 2B:
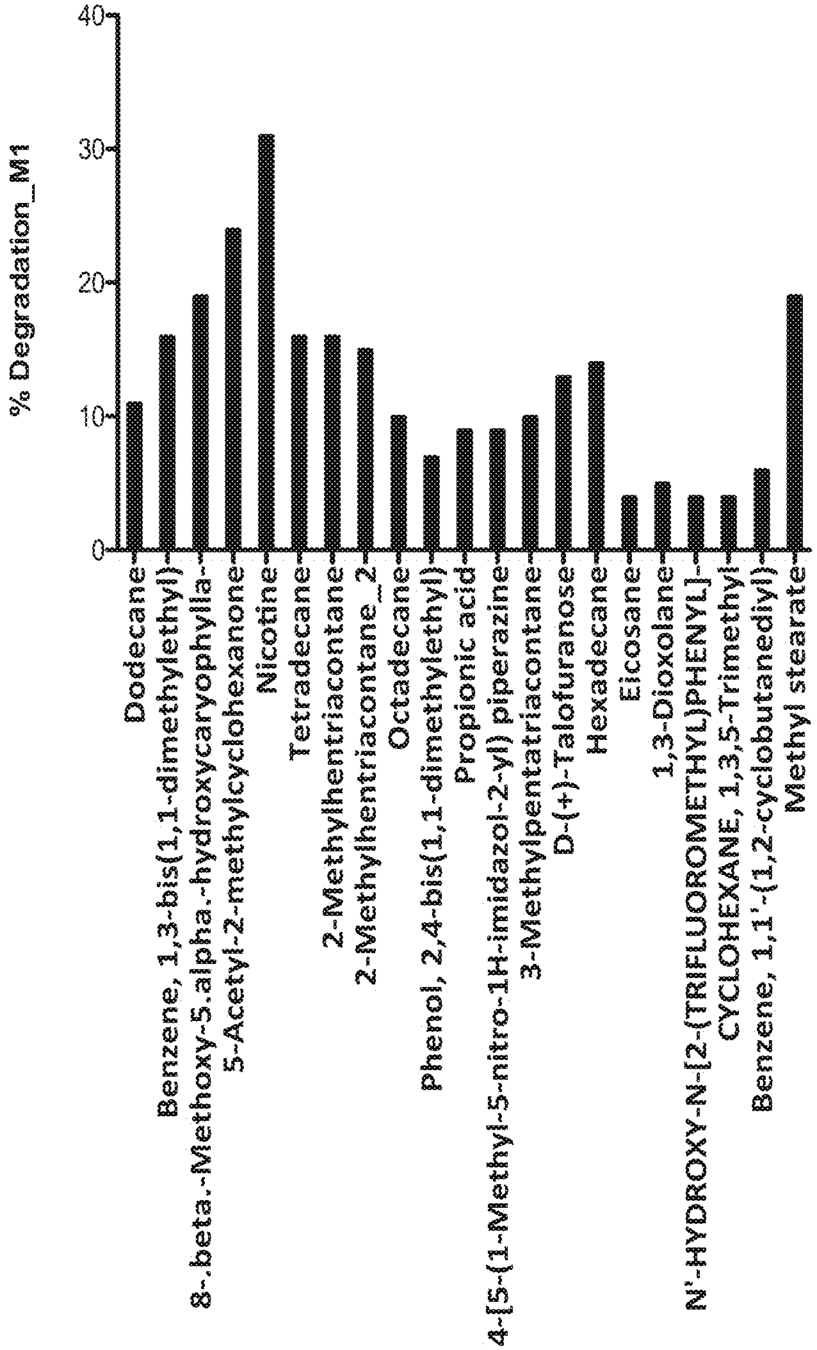
Figure 2C:
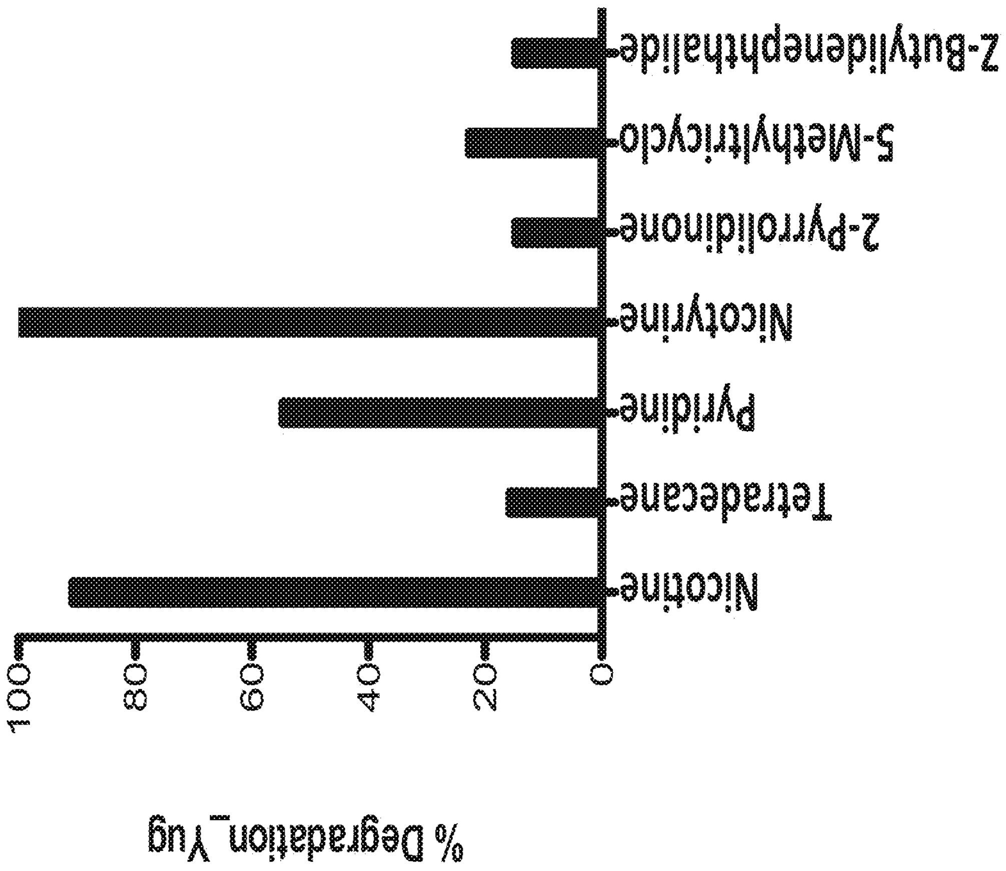
Figure 3A:
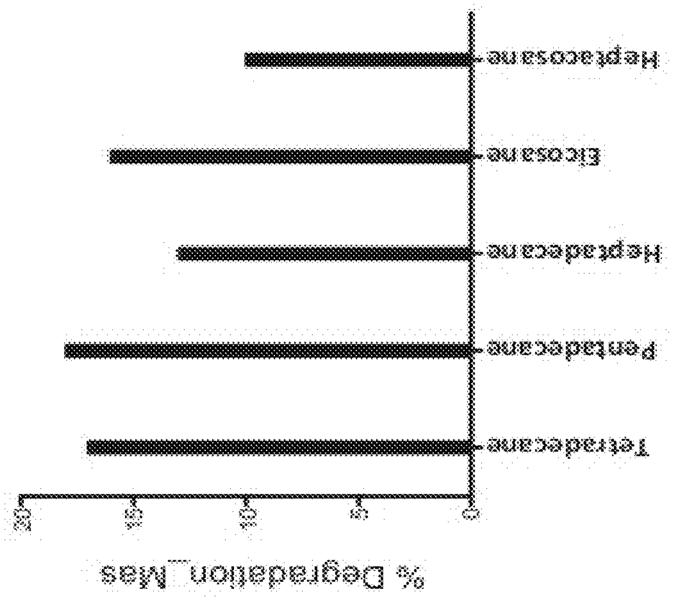
FIGS. 3A-B are bar graphs illustrating degradation of aliphatic hydrocarbons by Mas and Yug: GC-MS analysis of the degradation of a mixture of aliphatic hydrocarbons by Mas (A) and Yug (B) relative to minimal media with the same mixture of aliphatic hydrocarbons incubated with no bacteria. % degradation was calculated as in FIGS. 2A-C. The aliphatic mixture standards included: tetradecane, pentadecane, heptadecane, eicosane, heptacosane.
Figure 3B:
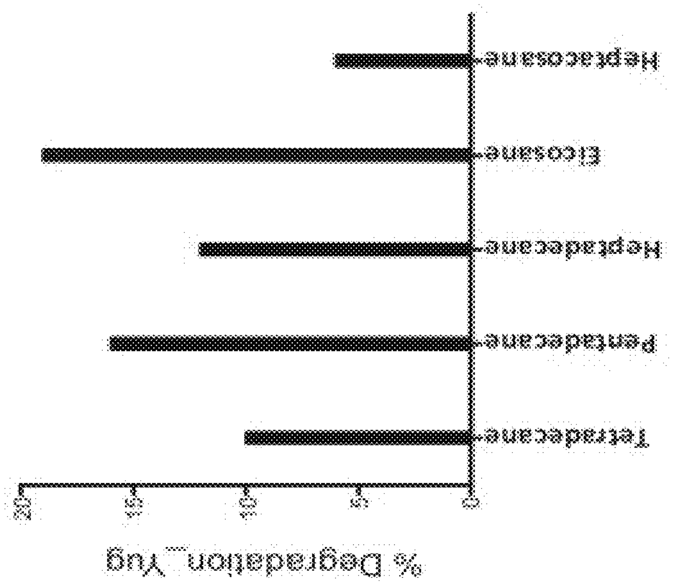
Figure 4A:
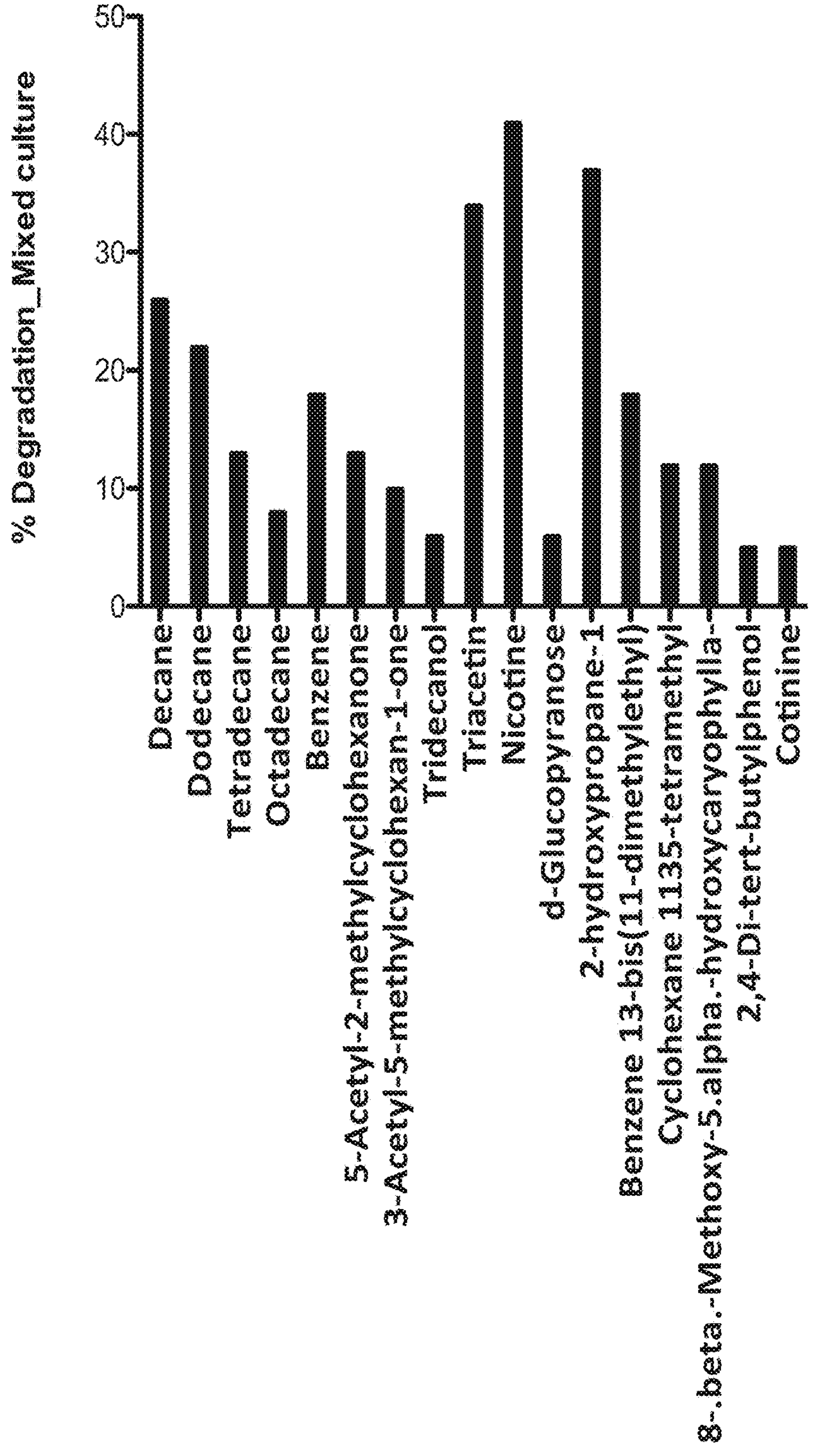
FIGS. 4A-B are bar graphs illustrating degradation of smoke residue and hydrocarbon standards by bacterial mixture: (A) GC-MS analysis of the degradation pattern of smoke residue by the mixture of M-1, Yug and Mas; (B) the degradation pattern of the same bacterial mixture of specific hydrocarbon standards, including: triacetate, nicotine, tetradecane, pentadecane, heptadecane, eicosane, and heptacosane (B). Columns represent percent degradation of the different compounds after growth for seven days relative to minimal media with smoke residue (MMS) or hydrocarbon standards, respectively, incubated with no bacteria.
Figure 4B:
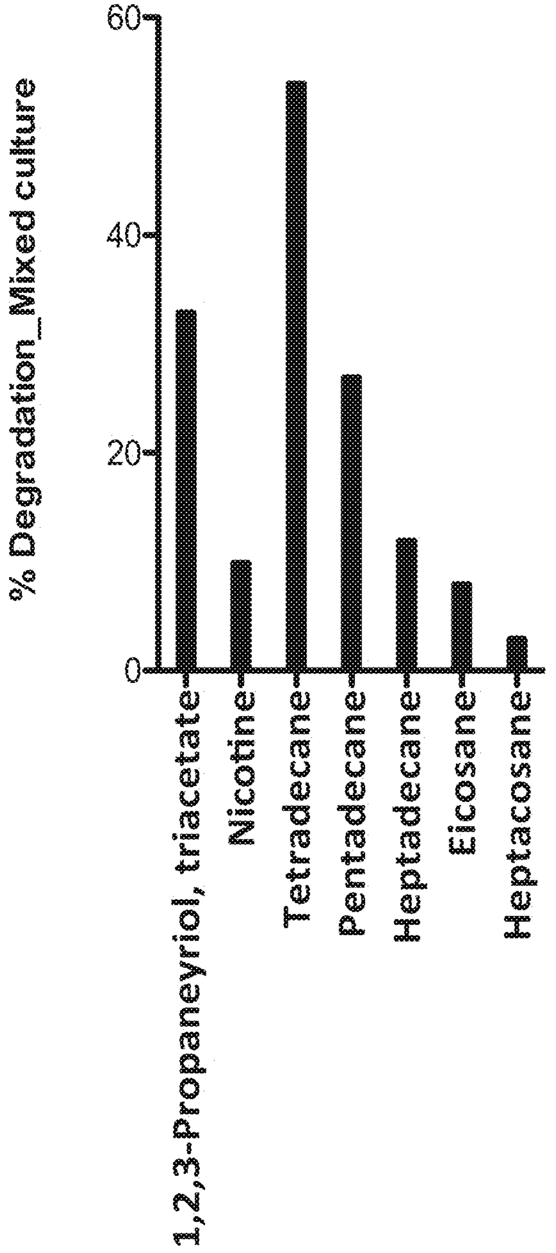

Each isolate (Mas, M-1 or Yug) was first incubated in MMS for four days, after which the cultures were extracted with a chloroform/methanol mixture. The separated organic phase then underwent GC-MS analysis. The comparison of the cultures to the control in each group demonstrated that Mas and M-1 can degrade a wide range of compounds in the smoke residue, including both cyclic and aliphatic alkanes (FIGS. 2A-B). Between these two bacteria, the Mas strain degraded the largest number of compounds, the most important being nicotine, tetradecane, triacetin, ethanone and methyl stearate. For M-1, the three most degraded compounds were nicotine, triacetin and decane. Although the Yug isolate (FIG. 2C) was able to degrade fewer compounds, it reduced more than 90% of the nicotine and nicotyrine. In all three cases, several new peaks appeared in the spectra of Yug, Mas and M-1, indicating that intermediate compounds are formed as a result of the degradation process.

The Yug (*Rhizobium pusense*) and Mas (*E. coli*) isolates were grown separately on a mixture of aliphatic hydrocarbons and separately on the polycyclic aromatic hydrocarbon benz(a)anthracene for a period of five days at 37° C. Both strains were able to break down from 10 to 20% of each of the aliphatic hydrocarbons in the mixture (FIGS. 3A-B), and 96% (Mas) and 62% (Yug) of the benz(a)anthracene (data not shown).

The three bacterial isolates were grown together on MMS and also on a defined hydrocarbon standard mixture for seven days at 37° C. The degradation pattern of the bacterial isolate mixture on smoke residue (FIG. 4A) demonstrates that it substantially reduced nicotine, triacetin and decane. The degradation pattern of the bacterial isolate mixture on the hydrocarbon standard mixture (FIG. 4B) shows that it significantly degrades tetradecane, pentadecane and triacetate (triacetin).

Example 2

Characterization of M-1 Smoke Residue Degrading Bacterium

M-1 was cultured in minimal media for 6 days at 37° C., with 3 different carbon sources:

1) 600 μl tar extract (3 repetitions) and 2 control cultures).
2) 200 μl alkane mix (3 repetitions) and 2 control cultures).
3) 200 μl non-alkane mix (3 repetitions)
4) Control culture with no carbon source (2 repetitions).

The cultures were extracted twice with chloroform: methanol after 6 days of growth and analyzed by GC-MS.

Results

Figure 5A:
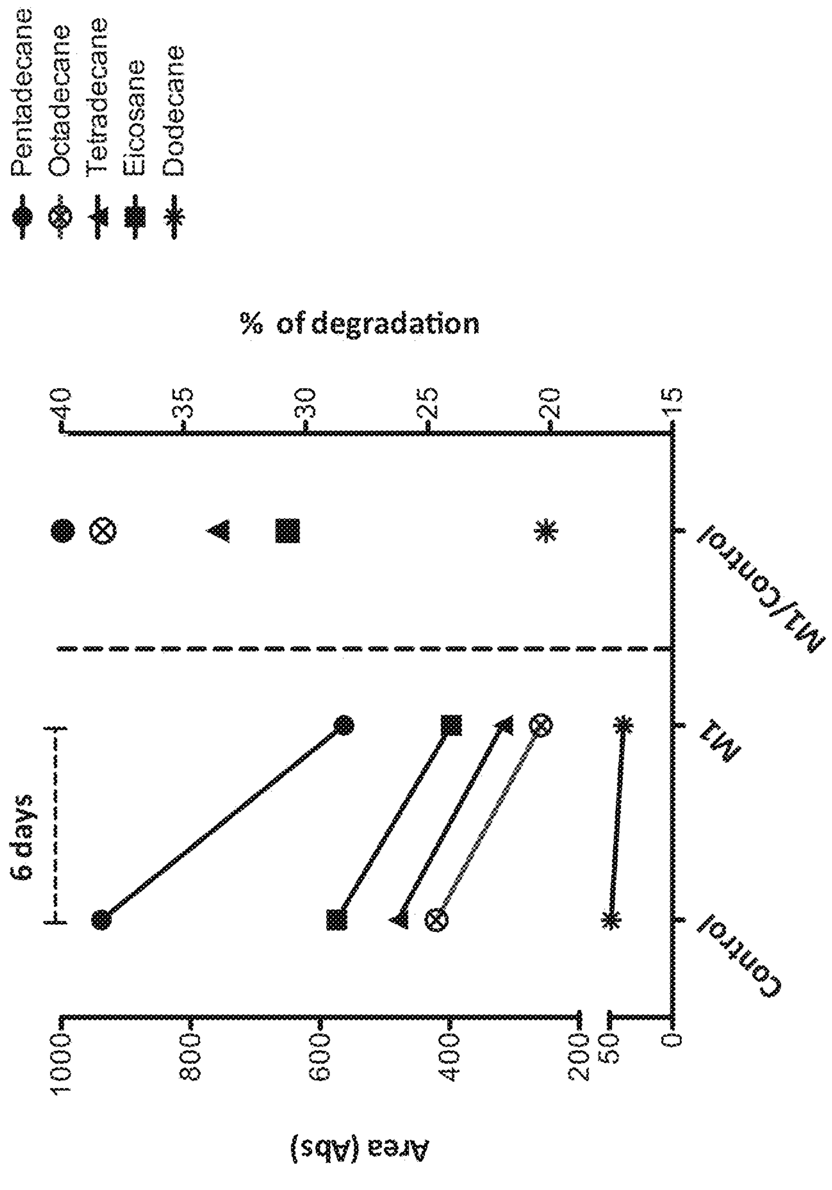
FIGS. 5A-B are graphs illustrating degradation of an alkane and a non-alkane mixture by isolate M-1: GC-MS analysis of the degradation pattern of an alkane mixture (dodecane, tetradecane, pentadecane, octadecane, eicosane) (A), and a non-alkane mixture (propanetriol triacetate, nicotine, benzene dimethyl ethyl, 2,4-di-tert-butylphenol, propanetriol 1-acetate, methyl stearate) (B) by M-1 isolate grown in MMS for 6 days at 37° C. The experiment was performed in triplicates. The plots (A, B) represent the integration area of the corresponding GC-MS peaks: control without the isolate M-1 compared to the M-1 cultures grown on the different hydrocarbons (left) and percent degradation of the different hydrocarbons by M-1 (right).
Figure 5B:
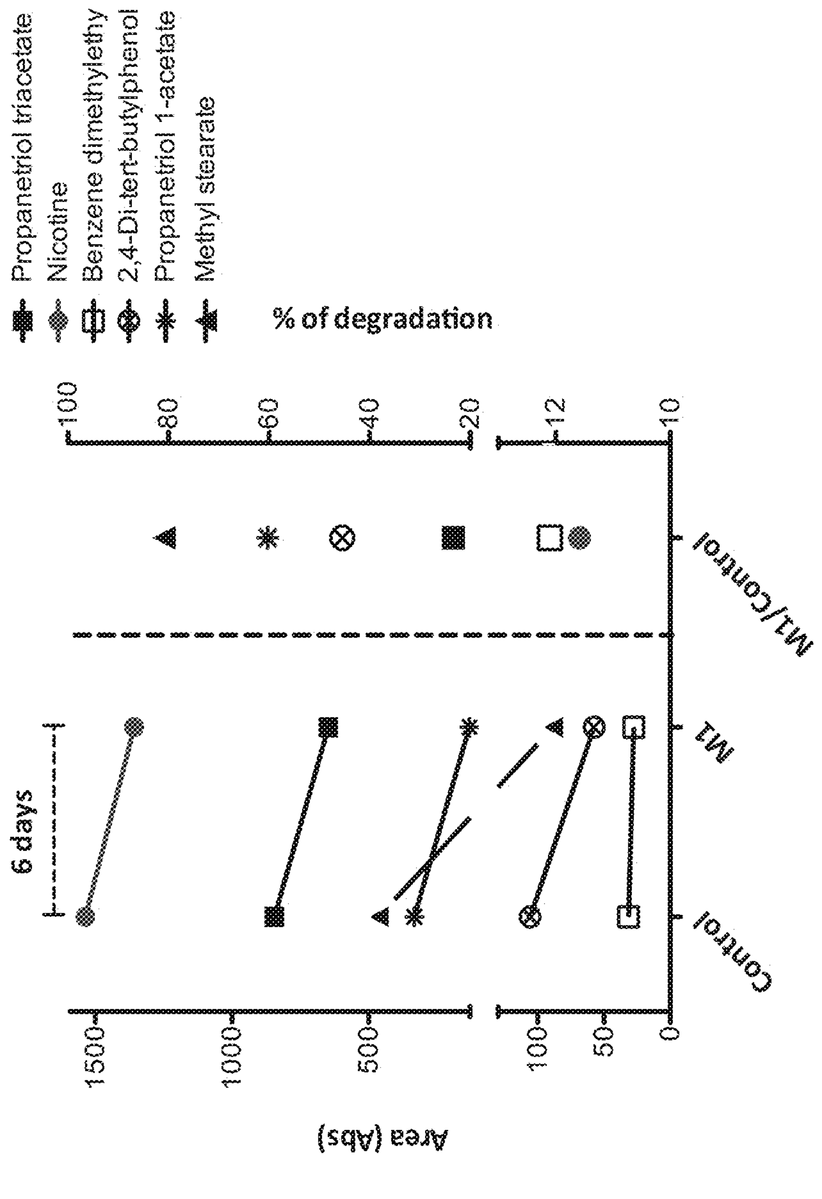

The results of the analysis are provided in FIGS. 5A-B. The plots demonstrate that among the alkanes, the medium-chain alkanes (C15) and (C18) were degraded to the greatest extent (~40%) while the longer and shorter chains were degraded to a lesser extent. Among the non-alkanes the methyl srearate (C18) was degraded the most (~80%), the short propanetriol (triacetin) (~60%) next, and almost 50% of the toxic 2,4-di-tert-butylphenol was also degraded. Benzene dimethyl ethyl and nicotine were degraded the least. The general conclusion would be that M-1 degrades best medium-long alkane chains. It seems that the isolate M-1 degrades slightly different substrates when growing on a mixture of standard alkanes as compared to when growing on the tar extract (compare with FIG. 2B).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A method of treating or preventing a disease associated with smoke residue in a subject or alleviating the symptoms caused by withdrawal from the use of nicotine, the method comprising administering to the subject a therapeutically effective amount of bacteria of a species selected from the group consisting of *Rhizobium pusense, Serratia marcescens* and *Pseudomonas aeruginosa*, thereby treating of preventing the disease associated with smoke residue or alleviating the symptoms caused by withdrawal from the use of nicotine.

2. The method of claim 1, wherein the smoke residue is on the fingers or in the respiratory system of the subject.

3. The method of claim 1, wherein the smoke residue is generated from tobacco smoking, marijuana smoking, environmental smoke, bonfire smoke, forest-fire smoke, airpit smoke, stove heater smoke, vehicle emission and air pollution.

4. The method of claim 1, wherein the subject smokes more than 1 cigarette a day.

5. The method of claim 1, wherein the method is for preventing a disease associated with smoke residue and the subject is not diagnosed with cancer.

6. A method of treating or preventing a disease associated with smoke residue in a subject or alleviating the symptoms caused by withdrawal from the use of nicotine, the method comprising administering to the subject a therapeutically effective amount of non-genetically modified bacteria of a species selected from the group consisting of *Rhizobium pusense, E. coli, Serratia marcescens* and *Pseudomonas aeruginosa*, thereby treating of preventing the disease associated with smoke residue or alleviating the symptoms caused by withdrawal from the use of nicotine.

7. The method or agent of claim 6, wherein said bacteria are of a species selected from the group consisting of *Rhizobium pusense* and *Serratia marcescens*.

* * * * *